US009966157B2

(12) United States Patent
Shilova et al.

(10) Patent No.: US 9,966,157 B2
(45) Date of Patent: May 8, 2018

(54) SOLID-LIQUID PROCESS FOR EXTRACTION OF RADIONUCLIDES FROM WASTE SOLUTIONS

(71) Applicant: Commissariat A L'Energie Atomique Et Aux Energies Alternatives, Paris (FR)

(72) Inventors: Ekatarina Shilova, Marseilles (FR); Pascal Viel, Meudon (FR); Vincent Huc, Orsay (FR); Yves Barre, Uchaux (FR)

(73) Assignee: Commissariat a L'Energie Atomique et aux Energies Alternatives, Paris (FR)

( * ) Notice: Subject to any disclaimer, the term of this patent is extended or adjusted under 35 U.S.C. 154(b) by 397 days.

(21) Appl. No.: 14/378,697

(22) PCT Filed: Feb. 22, 2013

(86) PCT No.: PCT/IB2013/051460
§ 371 (c)(1),
(2) Date: Aug. 14, 2014

(87) PCT Pub. No.: WO2013/124831
PCT Pub. Date: Aug. 29, 2013

(65) Prior Publication Data
US 2016/0042825 A1    Feb. 11, 2016

(30) Foreign Application Priority Data

Feb. 24, 2012  (EP) .................................... 12305221

(51) Int. Cl.
| | |
|---|---|
| *G21F 9/00* | (2006.01) |
| *G21F 9/12* | (2006.01) |
| *C22B 3/24* | (2006.01) |
| *B01J 20/22* | (2006.01) |
| *B01J 20/28* | (2006.01) |
| *B01J 20/30* | (2006.01) |
| *C07D 323/00* | (2006.01) |

(52) U.S. Cl.
CPC ................ *G21F 9/12* (2013.01); *B01J 20/22* (2013.01); *B01J 20/28011* (2013.01); *B01J 20/28023* (2013.01); *B01J 20/3085* (2013.01); *C07D 323/00* (2013.01); *C22B 3/24* (2013.01); *Y02P 10/234* (2015.11)

(58) Field of Classification Search
CPC .. B01J 20/28023; B01J 20/3085; B01J 20/22; B01J 20/28011; C22B 3/24; G21F 9/12
USPC ........... 423/2; 534/10; 549/348; 204/157.69; 588/20; 252/184
See application file for complete search history.

(56) References Cited

U.S. PATENT DOCUMENTS

| | | | |
|---|---|---|---|
| 5,132,345 A * | 7/1992 | Harris .................. | G01N 27/333 204/415 |
| 5,607,591 A | 3/1997 | Dozol et al. | |
| 6,075,130 A * | 6/2000 | Chen ................ | A61K 47/48707 423/9 |
| 6,174,503 B1 | 1/2001 | Moyer et al. | |
| 2003/0228974 A1* | 12/2003 | Katz .................... | B01J 20/3204 502/150 |
| 2009/0093664 A1 | 4/2009 | Wang | |
| 2010/0166624 A1* | 7/2010 | Raston .................. | B82Y 30/00 423/1 |

FOREIGN PATENT DOCUMENTS

| | | | |
|---|---|---|---|
| CN | 101538275 | * | 9/2009 |
| FR | 2 698 362 A1 | | 5/1994 |
| WO | WO 99/12878 A1 | | 3/1999 |

OTHER PUBLICATIONS

Translation of CN 101538275 A, Sep. 23, 2009.*
International Search Report and Written Opinion from corresponding International Application No. PCT/IB2013/051460, dated Sep. 9, 2013.
Alamarguy, et al.; *Surf Interface Anal.* 2008, 40, 802-805.
Asfari Z et al.; "A Tribenzo Modified 1,3-Calix[4]-bis-crown-6: A Highly Selective Receptor for Cesium"; *Tetrahedron Letters*, Elsevier, Amsterdam, NL; vol. 40, No. 4; Jan. 22, 1999; pp. 691-694; XP004151419.
Bahram, Mokhtari et al.; "A Review of Calixarene Applications in Nuclear Industries"; *Journal of Radioanalytical and Nuclear Chemistry*, Kluwer Academic Publishers, Do; vol. 287, No. 3; Oct. 26, 2010; pp. 921-934; XP019885998.
Belanger, et al.; *Chem. Soc.* Rev 2011, 40, 3995-4048.
Casnati; *J. Am. Chem. Soc.*, 2001, 123 (49), pp. 12182-12190.
Dinse et al; *Applied Radiation and Isotopes* 2000, 53, 381-386.
Duhart, et al.; *Journal of Membrane Science*, 185 (2001) 145-155.
Guillon, et al.; *J. Org. Chem.*, 2000, 65 (24) 8283-8289.
Incerti, et al.; *Chem Med Chem*, 2010, 5, 1143-1149.
Lyskawa , et al.; *J. Am. Chem. Soc.*, 2004, 126 (39), pp. 12194-12195.
Mokhtari et al.; *J Radioanal. Nucl. Chem.* (2011) 287:921-934.
Schank, K; *Diazonium and Diazo Groups* (1978); John Wiley & Sons, Ltd., 1978; pp. 645-657.
Shakir, et al.; "Removal of Cesium from Aqueous Solutions and Radioactive Waste Stimulants by CoPrecipitate Flotation"; *Separation and Purification Technology*; 54(3), 373-381.
Shakir, et al.; Flotation of Cesium Coprecipitated with Nickel Hexacyanoferrate(II) from Aqueous Solutions and Radioactive Waste Stimulants; *Separation Science and Technology*; 42(6), 1341-1365.
Viel et al.; *Applied Surface Science* 2007, 253, 3263-3269.

(Continued)

*Primary Examiner* — Steven Bos
(74) *Attorney, Agent, or Firm* — Alston & Bird LLP

(57) ABSTRACT

The invention related to a complexing system for extracting a radionuclide from a waste water solution including calix [n]arene groups on the surface of a porous conducting material.

14 Claims, 6 Drawing Sheets

(56) References Cited

OTHER PUBLICATIONS

Warin, et al.; Status of French Research Program on Partitioning and Transmutation; *Journal of Nuclear Science and Technology*, 2007, 44(3), 410-414.
Warin, et al.; Future Nuclear Fuel Cycles: Prospect and Challenges for Actinide Recycling; *IOP Conference Series: Materials Science and Engineering*, 9, 2010, 012063.

* cited by examiner

SOLID-LIQUID PROCESS FOR EXTRACTION OF RADIONUCLIDES FROM WASTE SOLUTIONS

FIELD

The invention relates to a complexing system for extracting radionuclides from waste solutions, notably cesium and strontium. The invention also relates to a method of preparation thereof, as well as to a method of use thereof.

BACKGROUND

The treatment of industrial liquid effluents contaminated by heavy metals has attracted intense interest in recent years, especially for nuclear waste remediation. Disposal of radioactive waste is horrendously expensive. As environmental, political and public health entities place more focus on Zero Liquid Discharge strategies, nuclear industry is now required to treat or eliminate waste streams to a much higher standard than ever before. An urgent need has arisen for new technologies to remove radionuclides such as highly toxic Cs137 producing only solid waste for disposal. The selective removal of Cs significantly reduces the toxicity of the residual waste and offers an opportunity of reutilization of radiocesium as a source of gamma radiation for several purposes both industrial and medical, for example to treat certain types of cancer or for industrial measurement gauges, including moisture, density, leveling, and thickness gauges etc.

Separations-technology development of nuclear wastes is ongoing for a half of century. Three main categories of methods are currently applied: liquid-liquid extraction, sorption and coprecipitation processes.

Sorption, also called ion-exchange chromatography is typically used for dilute solutions, to collect and concentrate species, when the use of organic solvents is not desired, and when the column media may be part of a final waste form (incorporation in a borosilicate glass). However, ion-exchange materials such as ammonium molybdophosphate and crystalline silicotitanate cannot sorb radionuclides such as Cs from highly concentrated and alkaline raw wastes. In addition, they generally exhibit a poor selectivity.

Coprecipitation processes consist in precipitating the radionuclide with a precipitant. As an example, cesium may be removed from liquid waste by coprecipitating it with hexacyanoferrates (HCFs) of divalent transition or heavy metal cations, such as ZnHCF[1] or NiHCF[2], and subsequent flotation of the precipitate. However, this method leads to quite large volumes of secondary wastes, namely inorganic sludges containing a high content of water. In addition, theses sludges can hardly be treated as they are chemically unstable.

Liquid-liquid extraction processes of radionuclide are typically used when a radionuclide(s) is to be separated from solutions with large concentrations of other metals. This method consist in contacting at countercurrent an aqueous waste solution with an immiscible organic solvent containing a complexing agent as extractant, such as tributylphosphate, tripyridyltriazine, bistriazinylpyridines (GANEX, PUREX, DIAMEX and SANEX processes)[3],[4], or calixarene crown ether (U.S. Pat. No. 6,174,503). However, in spite of its good selectivity, this method generally requires the use of organic solvents, acidification of the waste, which reveal costly. Further, the stripping procedure required to regenerate the immiscible organic solvent containing the loaded extractant leads to quite large volumes of liquid wastes (secondary liquid wastes), which may need to be further concentrated. In addition, extractant is generally progressively lost into the aqueous phases during the successive runs, thus further increasing the cost of liquid-liquid extraction processes.

A solid-liquid extraction method for removing cesium from model nuclear waste has also been reported (A. Duhart, et al., Journal of Membrane Science 185 (2001) 145-155). This method involves a solid membrane composed of an unsymmetrical calix[4]arenebiscrown-6 bonded to an immobilized polysiloxane backbone. However, the extraction efficiency of this membrane is much lower than that of liquid-liquid extraction process implementing the same calixarene and/or requires higher amounts of calixarene grafted in the solid phase. Further, the cesium/sodium selectivity is very low as compared to that of liquid-liquid extraction process.

Thus, there is a need for a method of treatment of radionuclides contaminated aqueous and/or organic solutions that overcome the drawbacks of the methods of the state of the art.

SUMMARY

It now has been developed a novel solid-liquid extraction method, called SOLIEX (for Solid-Liquid Extraction method) for removing radionuclides, notably cesium and strontium. This method relies on the use of a complexing system comprising a porous conducting material, notably a conducting-fiber material bearing one or more calix[n] arene groups on at least one of its surface.

This complexing system unexpectedly exhibit a high extraction efficiency and selectivity, and thus can be used for the treatment of wastes with a high concentration of competing alkali metal cations. Indeed, without willing to be bound to any particular theory, the conducting porous network, notably fibers network makes the calix[n]arene groups easy to reach, thus enabling both a rapid and direct capture and release of the radionuclide. In addition, still without willing to be bound to any particular theory, the porous network, notably the fibers network limit the steric hindrances around calix[n]arene groups, and hence the deformation of their complexing cavity, thereby preserving high extraction efficiency and selectivity as compared to liquid-liquid extraction processes.

As another advantage, the complexing system of the invention can be adapted and/or modulated by molecular engineering according to the radionuclide to be captured. Thus, the complexation properties of calixarene groups immobilized on the surface of the porous conducting material may vary according to the size of the macrocyclic core and/or to the substituents present on this core.

As another advantage, the complexing system of the invention can be easily and efficiently regenerated by using a cost effective stripping procedure, which limits further generation of waste. Thus, the radionuclide such as cesium and strontium can be released from the extractant by only applying an electric potential to the conducting fibers of the complexing system so as to induce an electrochemical polarization, without need of highly concentrated mineral acids and/or large amounts of stripping aqueous solutions.

As a further advantage, calixarene groups can be immobilized on the porous conducting material, in particular on a conducting-fiber material via strong covalent bonds, thus allowing the treatment of aqueous and/or organic waste solutions and limiting the loss of extractant (calixarene groups) into the liquid phase during the successive runs, notably at an industrial scale.

Another object of the present invention is to provide a method for preparing the complexing system according to the invention.

Another object of the present invention is to provide calixarene derivatives useful for the preparation of the complexing system according to the invention.

Another object of the present invention is to provide a method of extraction of radionuclides from a waste solution.

These and other objects, features and advantages of the complexing system of the invention will be disclosed in the following detailed description of the patent disclosure.

Complexing System

Thus, in a first aspect, the invention provides a complexing system comprising calix[n]arene groups immobilized on the surface of a porous conducting material. The calix[n] arene groups are notably covalently bonded to the surface of a porous conducting material The complexing system of the present invention is notably suitable for extracting a radionuclide from an aqueous and/or organic effluent.

As used herein, the term "radionuclide" refers to an atom with an unstable nucleus, which is a nucleus characterized by excess energy available to be imparted either to a newly created radiation particle within the nucleus or to an atomic electron. The radionuclide, in this process, undergoes radioactive decay, and emits gamma ray(s) and/or subatomic particles. These particles constitute ionizing radiation. Radionuclides occur naturally, and can also be artificially produced. Radionuclides notably include cesium (Cs) and strontium (Sr), lanthanides such as europium (Eu) and actinides such as thorium (Th), neptunium (Np) and americium (Am).

Conducting Material

As used herein, the terms "porous material" refer to a solid which structure contains pores, notably open pores, and which is fluid permeable. By "open porosity" is meant porosity formed from pores or spaces which open out and remains accessible to calixarenes and radionuclides present in solution. The porous material according to the invention includes notably macroporous and mesoporous materials. As used herein, materials referred to as mesoporous are solids which, within their structure, have pores having a size of typically between 2 and 80 nm, which is an intermediate between that of micropores and that of macropores. As used herein, a "macroporous material" refers to a material containing pores having a size greater than 80 nm, notably ranging from 80 nm 300 nm. Porous materials suitable for the invention notably include fiber materials, in particular sponges or felts. The porous material according to the invention is notably a self-supported material that can be converted into the form of a membrane, in particular a homogeneous and/or flexible membrane. Thus, the terms "porous material" may be used interchangeably with "porous membrane". It is to be noted that the porous materials suitable according to the invention do not include dispersable and/or particulate materials such as carbon powders (carbon black) or carbon nanotubes. Indeed, these materials cannot be converted into membranes and/or cannot be handled at an industrial scale. In addition, to be conductive, such particulate material must generally be compressed, thereby limiting both the fluid and electrical conductivity through the particulate material and preventing its use as a filtration medium.

As used herein, the terms "conducting material" mean an electrically conducting material, i.e a material which contains movable electric charges, notably electrons. Conducting materials are notably conductor or semiconductor materials. Examples of porous conducting materials include conducting-fiber materials, notably metallic fiber and carbon fiber materials.

As used herein, the wording "conducting-fiber material" means a material comprising or consisting of conducting fibers. The conducting-fiber material may notably comprise more than 50%, notably more than 75% by weight of conducting fibers, relative to the total weight of the conducting-fiber material. The conducting fibers are generally arranged to form an open, porous, fluid permeable membrane. The conducting fibers are generally entangled and/or may form a nonwoven, woven or knitted fabric (membrane).

As examples of metallic-fiber material, mention may be made of, stainless steel wool. As examples of carbon-fiber material mention may be made of carbon fibers, carbon papers, carbon felts or carbon sponges.

In accordance with a preferred embodiment, the fiber-conducting material is a nonwoven membrane comprising or consisting of conducting fibers, notably carbon fibers. Preferably, the fiber-conducting material is a carbon felt.

The porosity of the conducting-fiber material may range from 1% to 99%, preferably from 70% to 95%, the percentage value referring to the volume of vacuum relative to the total volume of the porous conducting material.

The flow velocity of the fluid, i.e the waste solution, through the porous conducting membrane is preferably above 20 m/h.

The pressure drop, i.e the decrease in pressure from the enter point of the fluid, to the exit point downstream is preferably less than 0.5 bar per meter.

Calix[n]arene Groups

Calixarenes are cyclic molecules made up of several ([n]) phenol units linked via methylene groups. The most common calixarenes, calix[4]arenes, calix[6]arenes, or calix[8] arenes contain 4, 6, or 8 phenolic units, respectively.

The complexation properties of calixarenes are related to the structure and/or the size of macrocyclic cavity. Thus calix[4]arene groups may be suitable for the complexation and extraction of cesium, while calix[6]arene and/or calix [8]arene groups are suitable for extracting strontium or americium (C. Dinse et al, Applied Radiation and Isotopes 2000, 53, 381-386; B. Mokhtari et al., J Radioanal. Nucl. Chem. (2011) 287:921-934; A. Casnati *J. Am. Chem. Soc.,* 2001, 123 (49), pp 12182-12190)).

These complexation properties may be modulated by varying the nature of the groups present on this molecule.

Calix[n] arene groups according to the invention notably include calix[n]arene-crown ether groups, in particular calix [4]arene-crown-6 ether, more particularly the 1,3-alternate calix[4]arene-crown-6 conformer, which has been disclosed as a specific ligand of cesium (Guillon et al., J. Org. Chem., 2000, 65 (24) 8283-8289).

The calix[n]arene group may be a calix[n]arene-crown ether groups of formula (A):

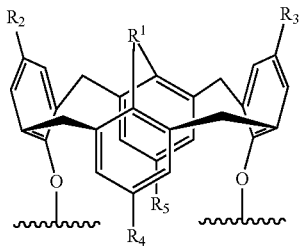

(A)

Wherein
R$_1$ is independently selected from —X(C$_2$H$_4$X)$_m$— or —X(C$_2$H$_4$X)$_{p/2}$YX(C$_2$H$_4$X)$_{p/2}$—,
X is independently selected from O and/or N;
m=3, 4, 5 or 6;
p=2 or 4;
Y is C$_3$-C$_{10}$ cycloalkylene or C$_6$-C$_{10}$ arylene; and
R$_2$-R$_5$ are each independently selected from H, or C$_1$-C$_6$ alkyl.

The porous conducting material may be coated with an organic layer comprising one or more calix[n]arene groups, which may be prepared from the polymerization of a monomer comprising calix[n]arene-crown ether groups, or by grafting said organic layer with calix[n]arene groups.

In a preferred embodiment, the calix[n]arene groups are covalently grafted on the surface of the porous conducting material, notably on the conducting-fiber material, preferably on the conducting fibers.

In yet a further embodiment, the calix[n]arene groups are grafted on the surface of the conducting-fiber material via a covalent bond —C(=O)NH—, —NH—C(=O)—, —C(=O)—O—, —OC(=O)—, —NH—CH$_2$—, —NH—CH$_2$— or —C—C. Preferably the calix[n]arene groups are grafted via-C(=O)NH—, —NH—C(=O)—, or —C—C bonds, which advantageously allow the complexing system to be used in highly basic media.

The calix[n]arene groups grafted onto the surface of the conducting-fiber material surface may be the same or different. Thus calix[n]arene groups having respectively a high selectivity for cesium and for strontium may both be grafted on the porous conducting material, notably on the conducting-fiber material surface.

Method of Preparation of the Complexing System

In a second aspect, the invention provides a method for preparing a complexing system as defined above, said method comprising:
i) Activating a porous conducting material, notably by applying an electric potential sufficient to allow the grafting of a radical precursor group;
ii) Reacting the activated conducting material with a compound of formula (II), thereby obtaining a modified conducting material;

W-L-V (II)

Wherein V is a radical precursor group;
L is a spacing group selected from (CH$_2$)$_r$, C$_3$-C$_{10}$ cycloalkylene or C$_3$-C$_{10}$ arylene;
W is selected from F, Cl, Br, I, OH, NHR$_{10}$, C(=O)H, C(=O)Hal, C(=O)OR$_9$;
R$_9$, R$_{10}$ are each independently selected from H or (C$_1$-C$_6$) alkyl,
r is an integer ranging from 1 to 20;
iii) Grafting the modified conducting material with a compound of formula (Ia):

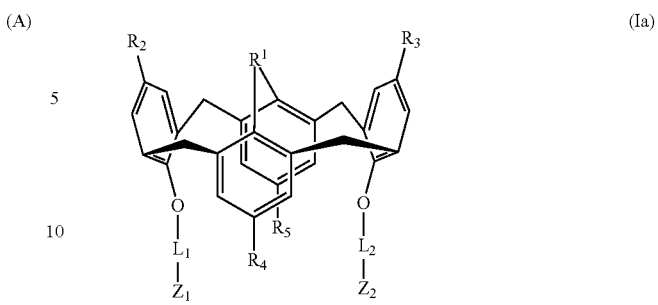

(Ia)

wherein:
R$_1$, R$_2$, R$_3$, R$_4$, R$_5$, are as defined above in formula (A);
L$_1$, L$_2$ are spacing groups and are each independently selected from —(CH$_2$)$_q$—, C$_3$-C$_{10}$ cycloalkylene or C$_3$-C$_{10}$ arylene;
Z$_1$, Z$_2$ are grafting groups and are each independently selected from F, Cl, Br, I, OH, NH$_2$, C(=O)H, C(=O)Hal, C(=O)OR$_8$;
R$_8$ is independently selected from H or (C$_1$-C$_6$)alkyl;
q is an integer ranging from 1 to 12;
thereby obtaining a complexing system as defined above.

In step i), the porous conducting material is activated as regards the grafting of a radical precursor group. As used herein, the term "activation" means that the porous conducting material has or reaches an electric potential sufficient to allow the grafting of the radical precursor group. This activation may be performed by applying an electric potential difference between the porous conducting material and a counter electrode. This potential difference may vary according to the nature of the radical precursor group to be grafted. Generally, a potential difference in the range of −2V to +2 V, notably of −1 V to +1 V is sufficient. As an example, when V is an aryldiazonium salt group (—C$_6$H$_4$—N≡N$^+$), the electric potential difference applied to the porous conducting material may range from +0.3 V to −1.0 V. Alternatively, this activation may occur spontaneously, in particular according to the nature of the electrode material and/or of the electrolytic middle. Thus, the rest potential of the porous conducting material may be sufficient to allow the grafting of the radical precursor group, without need of applying an electric potential difference.

As used herein, the wording "a radical precursor group" means a chemical group which is likely to catch or release an electron and thus to be converted into a radical species, that can react with the surface of the porous conducting material to form a covalent bond, notably a carbon-carbon or metal-carbon bond. By extension, the radical precursor groups also include precursors thereof. In that case, the method according to the invention further includes the step of converting said precursor into the corresponding radical precursor group.

Such an electrochemical reaction, which leads to the modification of the surface of the porous conducting material is called electrografting process.

Many functional groups suitable for electrografting processes have been disclosed in the litterature[5] and include notably the groups selected from carboxylate, amine, pyrrole, thiophene[6], aryldiazonium salt, acrylic acid and derivatives thereof.

As used herein, the term "derivatives" means that the electrografting groups including an aromatic or heteroaromatic ring may be substituted on said aromatic or heteroaromatic ring. Examples of substituents are notably OH, halogen atoms, $C_1$-$C_4$ alkyl, $C_1$-$C_4$ alkoxy.

The radical precursor groups such as thiophene or pyrrole can polymerize to form a conductive polymer coating on the surface of the porous conducting material. Advantageously, this polymerization leads to the formation of a polymer sheath around the fibers of the porous conducting material.

Preferred radical precursor groups include notably aryldiazonium (—$C_6H_4$—N≡$N^+$), —$NH_2$, —$COO^-$.

Preferably, the radical precursor group is an aryldiazonium ($C_6H_4$—N≡$N^+$) group or a precursor group thereof such as an arylamine (—$C_6H_4$—$NH_2$). Thus, the reduction of the diazonium group leads to a neutral but unstable radical that bonds to the surface as described in D. Alamarguy et al., Surf. Interface Anal. 2008; 40: 802-805.

The compounds of formula (II) wherein V is an aryldiazonium group may be easily obtained from the corresponding compound of formula (II) wherein V is $NH_2$. Diazotation of the amino groups may be performed according to methods well known in the art (Schank, K. In *Diazonium and Diazo Groups* (1978); John Wiley & Sons, Ltd., 1978; pp. 645-657).

The calix[n]arene ligands of formula (Ia) are then grafted onto the surface of the modified porous conducting material, via the covalent coupling of the grafting groups $Z_1$ and $Z_2$ with the W groups attached to the surface of the porous conducting material. As an example, $Z_1$, $Z_2$=$NH_2$ may react with W=COOH to form an amide bond (—C(=O)NH—).

In another embodiment, the present invention provides a method for preparing a complexing system as defined above, said method comprising the steps of:

i) Activating a porous conducting material, notably by applying an electrical potential sufficient to allow the grafting of a radical precursor group;

ii) Grafting the activated material with a compound of formula (Ib),

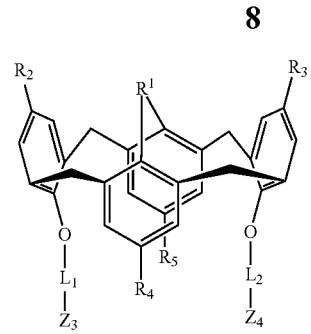

(Ib)

The reaction of radical precursor group V onto the surface of the porous conducting material may be performed as disclosed here above.

In a further aspect, the invention provides a complexing system obtainable according to any of the methods of preparation defined above.

Calix[n]arene Ligands

In yet a further aspect, the invention provides a compound of formula (Ia) or (Ib)):

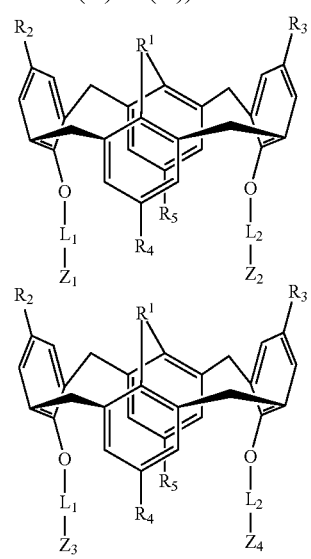

(Ia)

(Ib)

wherein $R_1$, $R_2$, $R_3$, $R_4$, $R_5$, $Z_1$, $Z_2$, $Z_3$, $Z_4$, $L_1$ and $L_2$ are as defined above.

The compounds of formula (Ia) or (Ib) may be notably selected from:

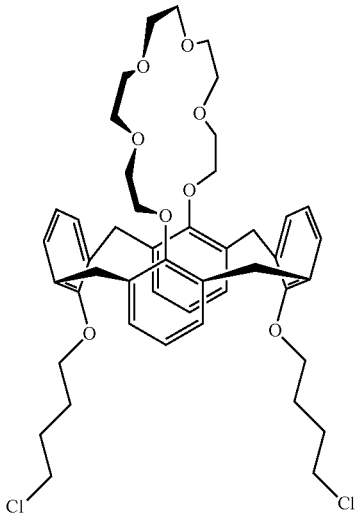

1

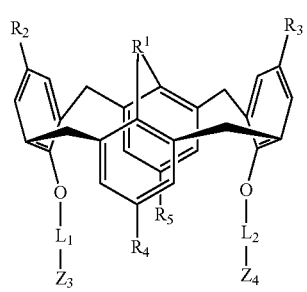

(Ib)

Wherein $R_1$, $R_2$, $R_3$, $R_4$, $R_5$, $L_1$ and $L_2$ are as defined above;

$Z_3$, $Z_4$ are each independently a group M-L-V,

M is independently selected from O or $NR_{10}$,

L, V and $R_{10}$ are as defined above in formula (II), thereby obtaining a complexing system as defined above.

-continued

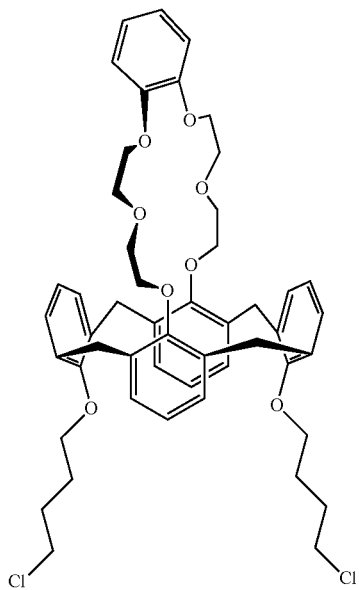

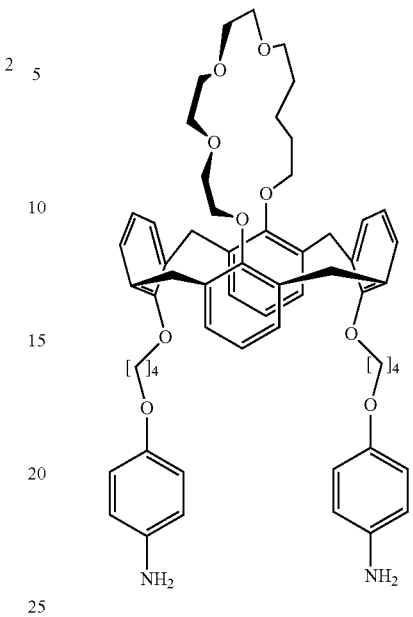

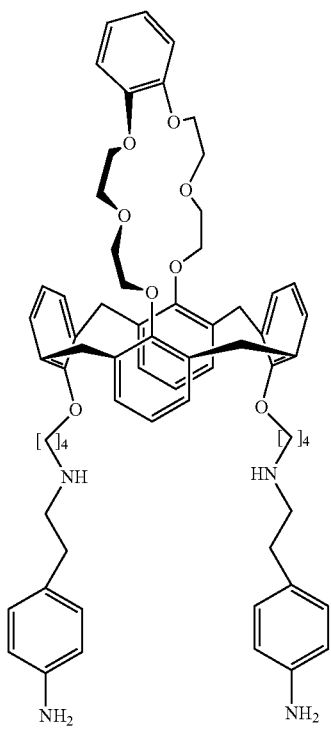

Method for Extracting Radionuclides from Waste Solution

In a further aspect, the invention provides a method for extracting radionuclides from a waste solution, said method comprising the steps of:
i) Contacting a volume of a waste solution with a complexing system as defined above; optionally
ii) Contacting the obtained radionuclide loaded complexing system with a volume of a stripping solution in acidic conditions, thereby removing the complexed radionuclide from said complexing system into the aqueous stripping solution, to make the complexing system available for reuse; and optionally
iii) Repeating steps i) and ii).

The radionuclide captured from the complexing system may be selected from cesium and/or strontium.

The complexing system may be a carbon-fiber material grafted by a 1,3-alternate calix[4]arene-crown-6 conformer.

The waste solution may be an aqueous or organic solution or a mixture thereof. The pH of the aqueous waste solution may be acid or basic and may notably range from 1 to 14. In a preferred embodiment, the aqueous waste solution is a basic waste solution.

Step i) may be performed by immersing the complexing system in the waste solution or by passing the waste solution over or through the complexing system.

Step ii) may be performed by contacting the complexing system containing a portion of complexed radionuclide with an aqueous stripping solution, in particular a dilute mineral acid.

In a preferred embodiment, the stripping is accomplished in step ii) by applying an electric potential on the porous conducting material of the complexing system. This electrostripping procedure advantageously helps reduce the volume of stripping solution needed to regenerate the complexing system, thereby reducing the amount of secondary waste to be treated, concentrated or stocked, and the costs of the extraction process.

Definitions

The following terms and expressions contained herein are defined as follows:

As used herein, the term "alkyl" refers to a straight-chain, or branched alkyl group having 1 to 6 carbon atoms, such as methyl, ethyl, propyl, isopropyl, butyl, isobutyl, sec-butyl, tert-butyl, pentyl, hexyl. Lower alkyl groups, which are preferred, are alkyl groups as defined above which contain 1 to 4 carbons. A designation such as "$C_1$-$C_4$ alkyl" refers to an alkyl radical containing from 1 to 4 carbon atoms.

As used herein, the term "alkoxy" refers to an alkyl-O— group, wherein said alkyl group is as defined hereabove.

As used herein, the term "Hal" refers to a halogen atom, namely Cl, Br, I or F, Cl and Br being preferred.

As used herein, the term "cycloalkyl" refers to a saturated or partially saturated mono- or bicyclic alkyl ring system containing 3 to 10 carbon atoms. Preferred cycloalkyl groups include those containing 5 or 6 ring carbon atoms. Examples of cycloalkyl groups include such groups as cyclopropyl, cyclobutyl, cyclopentyl, cyclohexyl, cycloheptyl, cyclooctyl.

As used herein, the term "aryl" refers to a mono- or bicyclic hydrocarbon aromatic ring system having 6 to 12 ring carbon atoms. Examples include phenyl and naphthyl. Preferred aryl groups include phenyl and naphthyl groups. Included within the definition of "aryl" are fused ring systems, including, for example, ring systems in which an aromatic ring is fused to a cycloalkyl ring. Examples of such fused ring systems include, for example, indane, indene, and tetrahydronaphthalene.

As used herein, the term "alkylene" means a straight or branched bivalent hydrocarbon chain having from 1 to 12 carbon atoms. The preferred alkylene groups are the lower alkylene groups having from 1 to about 4 carbon atoms. Exemplary groups include methylene and ethylene.

As used herein, the term "arylene" means a bivalent aryl group, as herein described.

As used herein, the term "cycloalkylene" refers to a bivalent cycloalkyl group as defined herein.

BRIEF DESCRIPTION OF THE DRAWINGS

Figures

DETAILED DESCRIPTION

Examples

Figure 1:
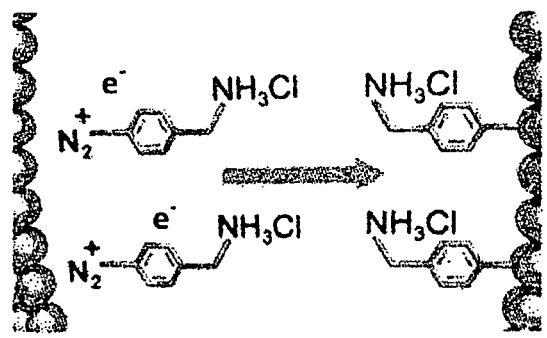
FIG. 1: The electrochemical deposition of diazonium salt on gold plate surface.

The following description and examples provide details of the manner in which the embodiments of the present invention can be made and used to effectively remove Cs from the contaminated solutions to be purified.

Calix[n]arene Ligand Synthesis.

A series of gold plates and carbon felts modified with calixarenes 1, 2 and 3 (Scheme 1) were prepared to accomplish the Cs complexation tests in water media.

Scheme 1. Calixarene 1, 2, and 3 structures.

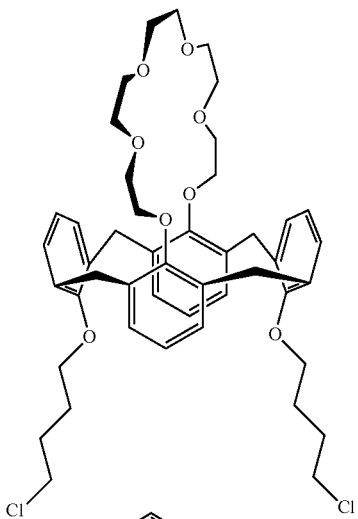

Calixarene 1

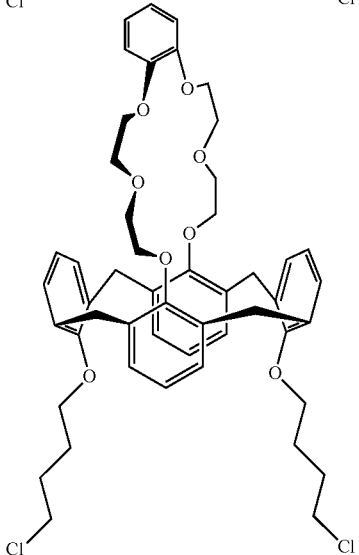

Calixarene 2

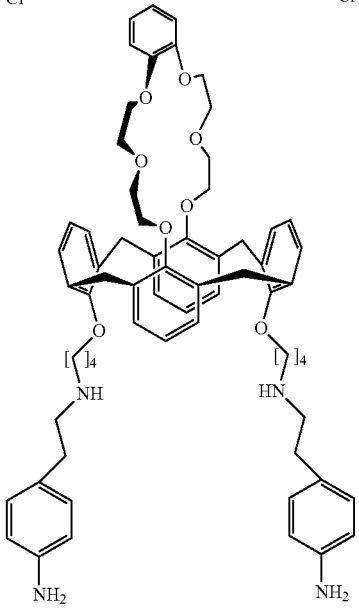

Calixarene 3

-continued

Calixarene 4

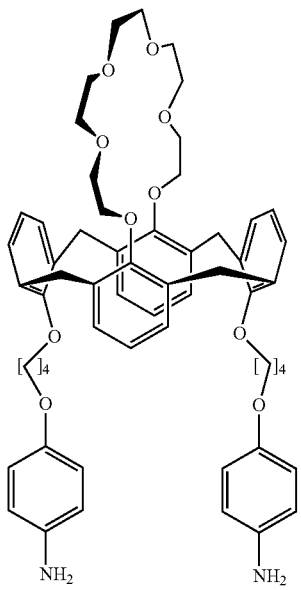

Synthesis of 1,3-alternate calix[4]arene-crown-6 Conformer with Cl Terminal Group (1 and 2)

The chloroderivatives of 1,3-dialkoxycalix[4]arene-crown-6 1 and 2 were synthesized from calix[4]arene according to the following sequence (Scheme 2). The chloroderivative of 1,3-dialkoxycalix[4]arene was prepared in a 72% yield by alkylation of the unsubstituted calix[4]arene with chlorobromobutane in the presence of 2.3 equivalent of $K_2CO_3$ as a base, in refluxing $CH_3CN$ according to the classical methods of O-alkylation (J. Guillon, J.-M. Léger, P. Sonnet, C. Jarry, and M. Robba, *J. Org. Chem.* 2000, 65, 8283-8289). Further treatment with appropriate glycol ditosylate and an excess of $Cs_2CO_3$ in refluxing $CH_3CN$ gave the calix[4]arenes-crown-6 1 and 2 in the 1,3-alternate conformation.

Scheme 2. Calixarene 1 and 2 synthesis.

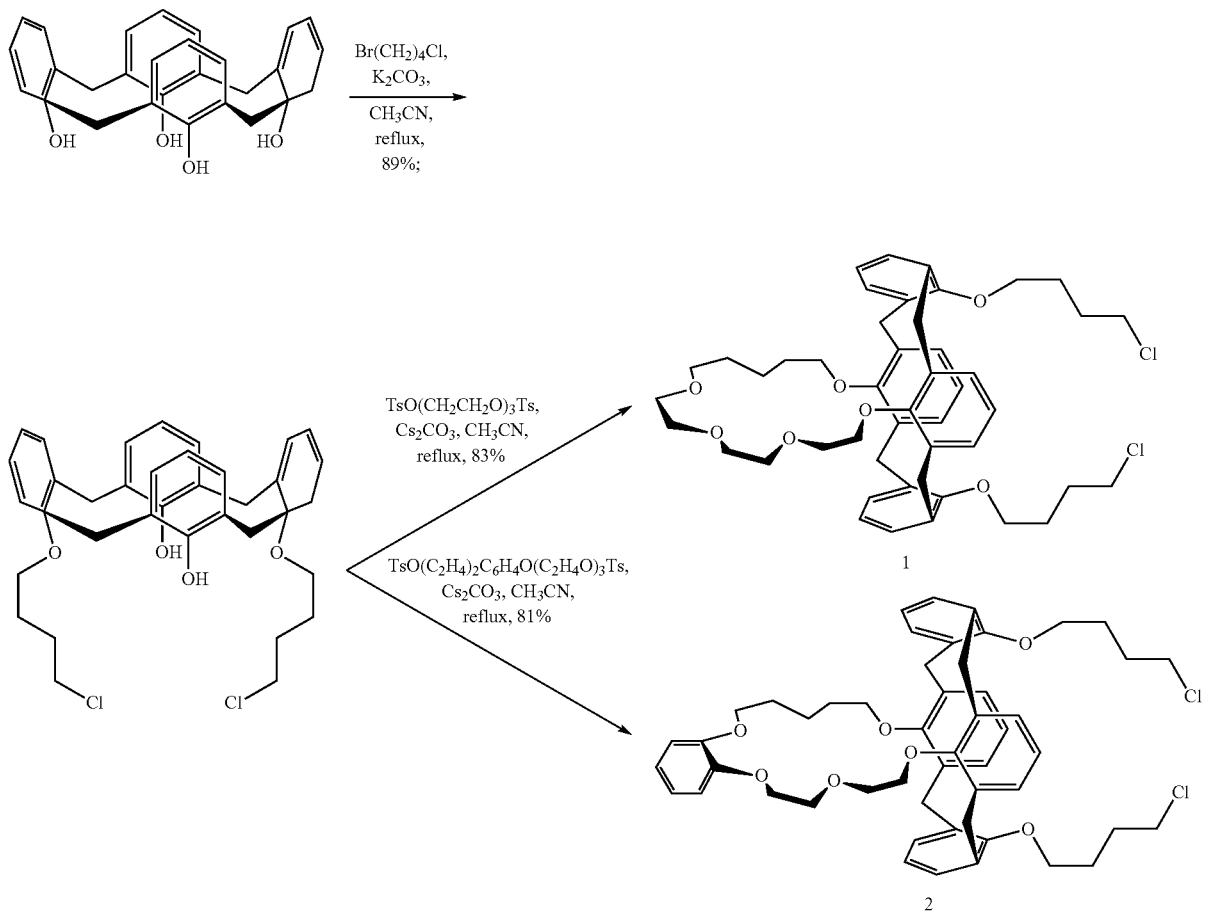

Synthesis of chloroderivative of 1,3-dialkoxycalix[4]arene

To a suspension of calix[4]arene (4.71 mmol, 1.0 g) in CH$_3$CN (100 mL) were added bromochlorobutane (23.56 mmol, 2.71 ml) and K$_2$CO$_3$ (4.71 mmol, 0.651 g) and the reaction mixture was stirred under reflux for 12 h. The solvent was then removed under reduced pressure and the residue quenched with 100 mL of 10% HCl and 200 mL of CH$_2$Cl$_2$. The organic phase was separated and washed twice with distilled water (2×100 mL) and 100 ml of brine. CH$_2$Cl$_2$ was dried over Mg$_2$SO$_4$ and distilled off to afford a solid which was crystallized from ⅕ CH$_2$Cl$_2$-MeOH to give pure chloroderivative of 1,3-dialkoxycalix[4]arene: yield 89%; $^1$H NMR (CDCl$_3$) δ 7.94 (s, 2H, OH), 7.06 and 6.89 (d, J=7.34 Hz, 4H each, ArH meta), 6.76-6.63 (m, 4H, ArH para), 4.26 (d, J=13.0 Hz, 4H, ArCH$_2$Ar), 4.05-4.01 (m, 4H, CH$_2$O), 3.78-3.74 (m, 4H, CH$_2$Cl), 3.39 (d, J=13.0 Hz, 4H, ArCH$_2$Ar), 2.26-2.18 (m, 8H, CH$_2$). HRMS (CI, NH$_3$): M Calcd. 624.6 (MNH$_4^+$), found 624.3.

Synthesis of 1,3-alternate calix[4]arene-crown-6 Conformer with Cl Terminal Group 1 and 2

Chloroderivative of 1,3-dialkoxycalix[4]arene (0.425 g; 1.00 mmol), K$_2$CO$_3$ (1.380 g; 10.00 mmol), ditosylate (0.691 g; 1.00 mmol), and acetonitrile (100 mL) were refluxed for 12 h. The solvent was then removed under reduced pressure and the residue quenched with 100 mL of 10% HCl and 200 mL of CH$_2$Cl$_2$. The organic phase was separated and washed twice with distilled water (2×100 mL) and 100 ml of brine. CH$_2$Cl$_2$ was dried over Mg$_2$SO$_4$ and distilled off to afford a solid which was crystallized from ⅕ CH$_2$Cl$_2$-Me$_3$CN to give pure 1,3-alternate calix[4]arene-crown-6 conformer with Cl terminal group 1: yield 83%; $^1$H NMR (CDCl3) δ 7.08 and 7.02 (d, J=7.50 Hz, 4H each, ArH meta), 6.87-6.80 (m, 4H, ArH para), 3.79-3.29 (m, 36H, 8H, ArCH$_2$Ar, 4H, CH$_2$O, 4H, CH$_2$Cl, 20H, OCH$_2$CH$_2$O), 1.61-1.57 (m, 4H, CH$_2$), 1.45-1.37 (m, 4H, CH$_2$). HRMS (CI, NH$_3$): M Calcd. 824.8 (MNH$_4^+$), found 824.6.

The 1,3-alternate calix[4] arene-crown-6 conformer 2 was synthesized in the same manner using appropriate glycol ditosylate prepared according to described procedure (Z. Asfari, V. Lamare, J.-F. Dozol, and J. Vicens, *Tetrahedron Letters* 1999, 40, 691-694). Yield 61%; $^1$H NMR (CDCl$_3$) δ 7.06-7.02 (m, 8H, calix ArH meta), 6.99 (br S, 4H, calix ArHpara), 6.83 (t, 7.50 Hz, 2H benzoArH), 6.68 (t, 6.68 Hz, 2H benzoArH), 4.13-4.11 (m, 4H, CH2O), 3.78 (s, 8H, ArCH$_2$Ar), 3.69-3.67 (m, 4H, CH2Cl), 3.58-3.44 (16H, OCH$_2$CH$_2$O), 1.64-1.60 (m, 4H, CH$_2$), 1.50-1.44 (m, 4H, CH$_2$). HRMS (CI, NH$_3$): M Calcd. 872.8 (MNH$_4^+$), found 872.5.

Synthesis of 1,3-alternate calix[4]arene-crown-6 Conformer with Terminal Aromatic Amino Group (3)

Calixarene 3 was prepared from chloroderivative 2 applying the classic conditions (M. Incerti et al, *Chem Med Chem*, 2010, 5, 1143-1149) to react the primary aliphatic amine and halogen and was used for construction of complexing system without purification.

Synthesis of 1,3-alternate calix[4]arene-crown-6 Conformer with Terminal Aromatic Amino Group (4)

Calixarene 4 was prepared from 1 equivalent of chloroderivative 1 and 2.2 equivalents of paranitrophenol in DMF in the presence of 4 equivalents of K$_2$CO$_3$ as a base. Then the reaction was quenched with 100 mL of 10% HCl and 200 mL of CH$_2$Cl$_2$. The organic phase was separated and washed twice with distilled water (2×100 mL) and 100 ml of brine. CH$_2$Cl$_2$ was dried over Mg$_2$SO$_4$ and distilled off to afford a solid which was reduced to the amine with H$_2$/Pd catalyst and was used for construction of complexing system without purification.

Construction of the Complexing System.

Electrochemical Modification of the Conducting-Fiber Material with Organic Compounds The electrochemical deposition of organic compound to conducting-fiber material was accomplished on gold plates to have an opportunity to confirm the results of deposition by ATR analysis.

The electrochemical deposition (D. Alamarguy, A. Benedetto, M. Balog, S. Noel, P. Viel, F. Le Derf, F. Houze, M. Sallé and S. Palacin, *Surf. Interface Anal.* 2008, 40, 802-805) of hydrochloride salt of 4-aminoethylbenzene diazonium tetrafluoroborate (FIG. 1) was carried out with an EGG-PAR 273 potentiostat in three-electrode electrochemical cell under a highly controlled (argon purified) atmosphere inside a glove box. The working electrodes were the gold substrates.

Figure 2:
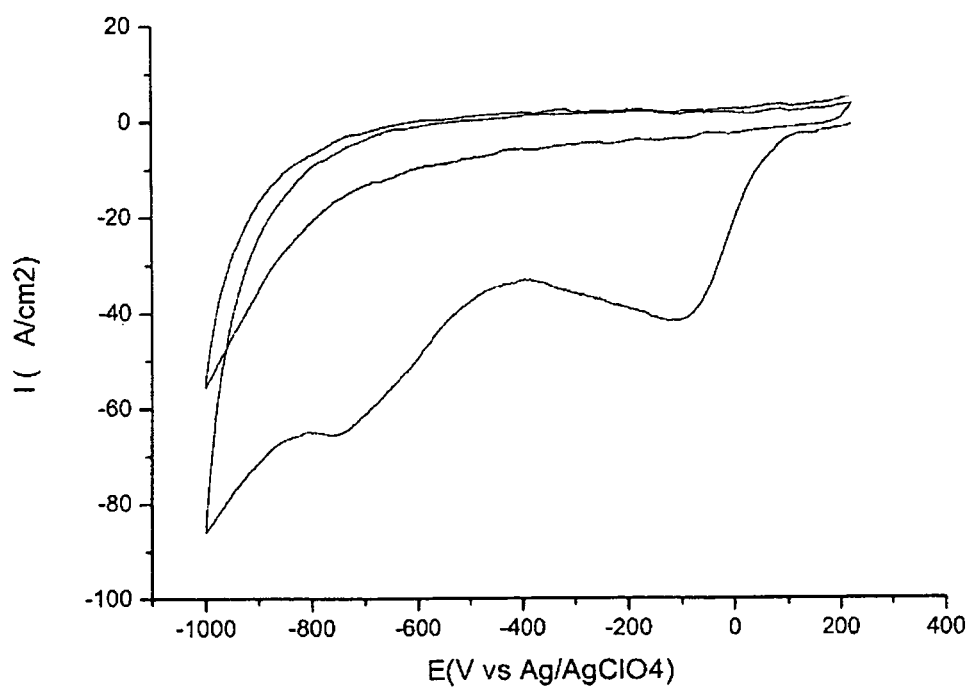
FIG. 2: Current-potential characteristic recorded during grafting of diazonium salts on gold substrate.

The reference electrode was based on the Ag|Ag$^+$ 10$^{-2}$ M couple. Electrochemical analysis was done using an EG&G potentiostat, model 273 A. A solution of 5 mM of diazonium salts in anhydrous acetonitrile was used; tetraethyl ammonium perchlorate 0.05 M was used as supporting electrolyte. Two cycles of potential sweep at 20 mV.s$^{-1}$ were carried out between the equilibrium potential (typically of the order of 0.3 V) and −1.0 V (FIG. 2). The results of deposition were confirmed by ATR analysis.

Carbon felts are preferred conductive material to form the complexing system. Carbon felts of 200 mg were modified in the same manner to create a demonstration sample for further extraction tests.

Figure 3:
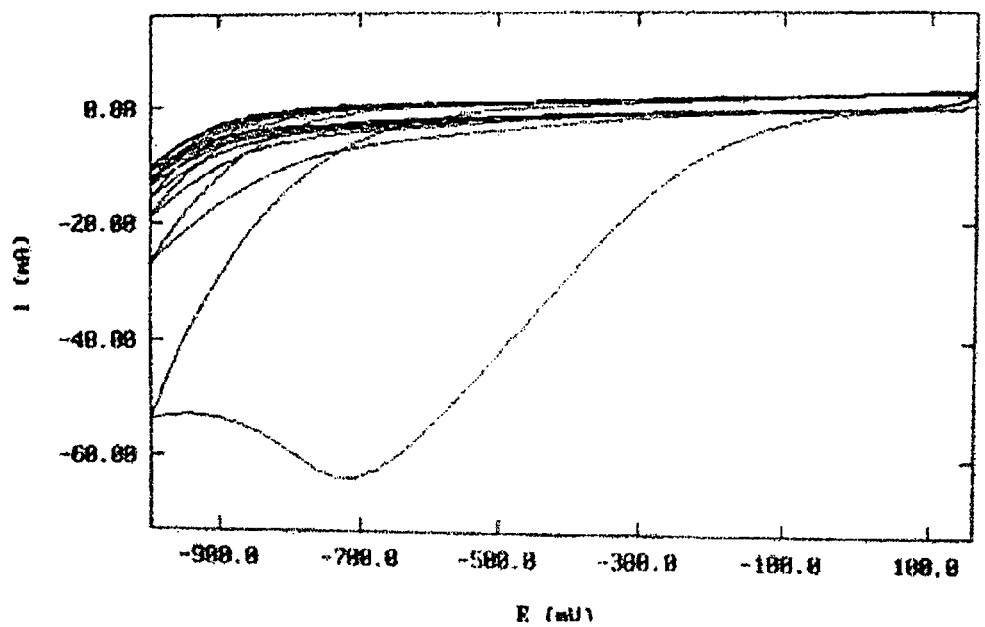
FIG. 3: Current-potential characteristic recorded during grafting of diazonium salts on carbon felts.

The electrochemical deposition of tetrafluoroborate of 4-aminoethyl benzene diazonium tetrafluoroborate was carried out with an EGG-PAR 273 potentiostat in three-electrode electrochemical cell under a highly controlled (argon purified) atmosphere inside a glove box. Three graphite bars for mechanical pencils Bic Criterium HB of 2 mm in diameter were used as power feed. The carbon felts were introduced to electrochemical cell and pierced with graphite bars for about 100% of their thickness. The reference electrode was done by a platinum wire. 126 mg of diazonium salts was placed to the electrochemical cell; tetraethyl ammonium perchlorate 0.05 M was used as supporting electrolyte. Six cycles of potential sweep at 20 mV s$^{-1}$ were carried out between the equilibrium potential and −1.0 V. The voltammograms of grafting process of diazonium salts on the carbon felt surface are represented in FIG. 3.

Electrochemical Deposition of the Calixarene 3 on the Surface of the Conducting Material The electrochemical deposition of calixarene-amine 3 (Scheme 1) on gold plates was carried out with an EGG-PAR 273 potentiostat in three-electrode electrochemical cell under a highly controlled (argon purified) atmosphere inside a glove box. The working electrodes were the gold substrates. The reference electrode was based on the Ag|Ag+ 10-2 M couple. Electrochemical analysis was done using a EG&G potentiostat, model 273 A. A solution of about 1 mM of diazonium salts in anhydrous acetonitrile was prepared directly in the electrochemical cell in presence of 1 equivalent of NOBF$_4$ by one equivalent of amine group; tetraethyl ammonium perchlorate 0.05 M was used as supporting electrolyte. Two cycles of potential sweep at 20 mV s$^{-1}$ were carried out between the equilibrium potential (typically of the order of 0.3 V) and −1 V. The presence of calixarene 3 on gold plates was confirmed by ATR analysis.

Electrochemical Deposition of the Calixarene 4 on the Surface of the Conducting Material.

The diazonium salt of calixarene 4 was obtained by diazotation in classic conditions and then the molecules were bonded to conducting surfaces by the electrochemical reduction of diazonium groups.

Figure 4:
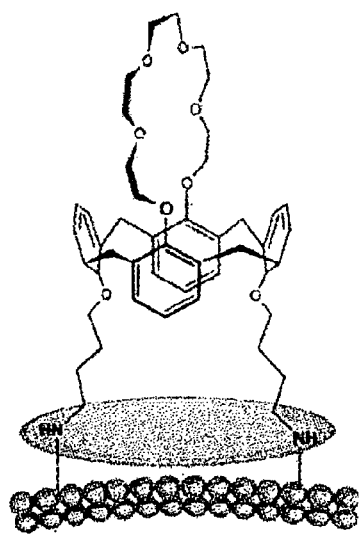
FIG. 4: Calixarene 1 grafted to the gold surface.
Figure 5:
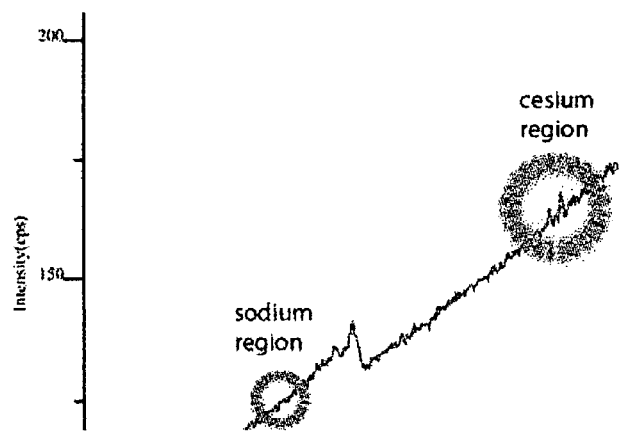
FIG. 5: XPS scans of the Na+ and Cs+ regions for gold surface containing calixarene 3.

Chemical Deposition of Calix[n]arene Ligands 1 and 2 on the Surface of the Conducting Material Calixarenes 1 and 2 were grafted on premodified gold surfaces (FIG. 4) via classical reaction between its Cl and surface terminal amino groups in the presence of $K_2CO_3$ and DMF (the same protocol was applied for synthesis of 3). The presence of calixarenes 1 and 2 on the surfaces of gold plates was confirmed by ATR analysis.

Calixarenes 1 and 2 were then grafted onto carbon felts surfaces via reaction between its Cl and surface $NH_2$ terminal groups in the presence of $K_2CO_3$ and catalytic amount of KI in DMF under argon at 80° C. during 24 h. Then carbon felts were washed in demineralized water during 12 h, acetonitrile (12 h), dichloromethane (30 min) and dried under vacuum for 1 hour.

Extraction of Cs.

Extraction of Cs by Gold Plates Containing Calixarenes 1, 2 and 3 from Water Media in Presence of High Excess of Na Ions The calixarene modified gold plates were kept in 3 ml of selectivity test solution during 12 h at RT in 3 ml glass bottles. The complexed gold plates were then washed with demineralized water, acetonitrile and dichloromethane and dried under vacuum. The XPS analysis indicated the presence of $Cs^+$ ions in all examined surfaces. The XPS results are collected in Table 1.

The selectivity coefficient may be expressed as:

$$S = R1/R2$$

where R2 is the final average equivalent ratio of Na+/Cs+ ions on the 1 mm$^2$ of surface of gold plate (determined from 3 different regions of the same plate), R1 is the initial equivalent ratio of Na$^+$/Cs$^+$ ions in the selectivity test solution calculated from Na$^+$ and Cs$^+$ concentrations. Selectivity test solution contained 4 mol/l of $NaNO_3$ and $5\times10^{-3}$ mol/l of $CsNO_3$ in demineralized water. Consequently, R1 (the initial ratio of Na$^+$/Cs$^+$ ions)=800.

TABLE 1

$$S = \frac{[Na]_i}{[Na]_f} \times \frac{[Cs]_f}{[Cs]_i}$$

i—initial concentration
f—final concentration
Calculated average ratios of Na+/Cs+ ions (R2) for 1 mm of the sample surface and selectivity (S) in all samples.

| Experiment code | Calixarene | R1 | R2 | S |
|---|---|---|---|---|
| Gold plates: | | | | |
| | 2 | 800 | | very little quantity of Na+ was found => S >> 1000 |
| | 1 | 800 | 1.68 | 476.2 |
| | 3 | 800 | | Na$^+$ wasn't found (FIG. 6) => S = ∞ |

Extraction of Cs by Carbon Felts Containing Calixarenes 1, 2 and 3 from Water Media in Presence of High Excess of Na Ions Calixarenes 1 and 2 were grafted onto carbon felts surfaces via reaction between its Cl and surface $NH_2$ terminal groups in the presence of $K_2CO_3$ and catalytic amount of KI in DMF under argon at 80° C. during 24 h. Then carbon felts were washed in demineralized water during 12 h, acetonitrile (12 h), dichloromethane (30 min) and dried under vacuum for 1 hour.

The calixarene modified carbon felts 1 and 2 were kept in 3 ml of selectivity test solution described above during 24 h at RT in 3 ml glass bottles. The complexed carbon felts were then washed with demineralized water (12 h), acetonitrile (12 h), dichloromethane (1 h) and dried under vacuum (12 h). The XPS analysis indicated the presence of $Cs^+$ ions inside and outside in all examined surfaces. The average results are collected in Table 2.

TABLE 2

Calculated average ratios of Na+/Cs+ ions (R2) for 1 mm of the sample surface and selectivity (S) in all samples.

| Experiment code Carbonfelts: | Calixarene | R1 | R2 | S |
|---|---|---|---|---|
| Carbonfelt 1 (outside) | 1 | 800 | 10.78 | 74.21 |
| Carbonfelt 1 (inside) | 1 | 800 | 10.43 | 76.7 |
| Carbonfelt 2 (outside) | 2 | 800 | 13.57 | 58.95 |
| Carbonfelt 2 (inside) | 2 | 800 | 7.38 | 108.40 |

The results presented in Tables 1 and 2 for $R_2$ (the final average equivalent ratio of Na+/Cs+ ions on the 1 mm$^2$ of surface) demonstrate that the calixarenes grafted on surface are capable to perform the selective complexing of Cesium. $R_2$ and S are performance criteria of the complexing system: the decrease in R2 in correlation to R1 and the increase of S (selectivity) will indicate better system performance. The analysis of these values shows that the selectivity of calixarene 2 modified with benzene moiety in its crown part (calixarenes 2 and 3) is in most cases better than selectivity of non-modified calixarene 1: these results are in accordance with data previously obtained by Dozol et al. (FR 2760236 A1) for liquid-liquid extraction of Cs ions by related calixarenes.

On the other hand, sodium is common laboratory impurity most frequently detected in XPS analysis occurring due to environmental or human impacts. For carbon felts it may also be the result of insufficient washing from non-complexed Na+ ions or may remain with residual traces of water or organic solvents employed in post complexation work-up. Further Cs extraction examples are made in deuterated organic media and show absolute selectivity of calixarene of this type for $Cs^+$ ions confirmed by $Cs^{133}$ and $Na^{23}$ NMR analysis.

Figure 6:
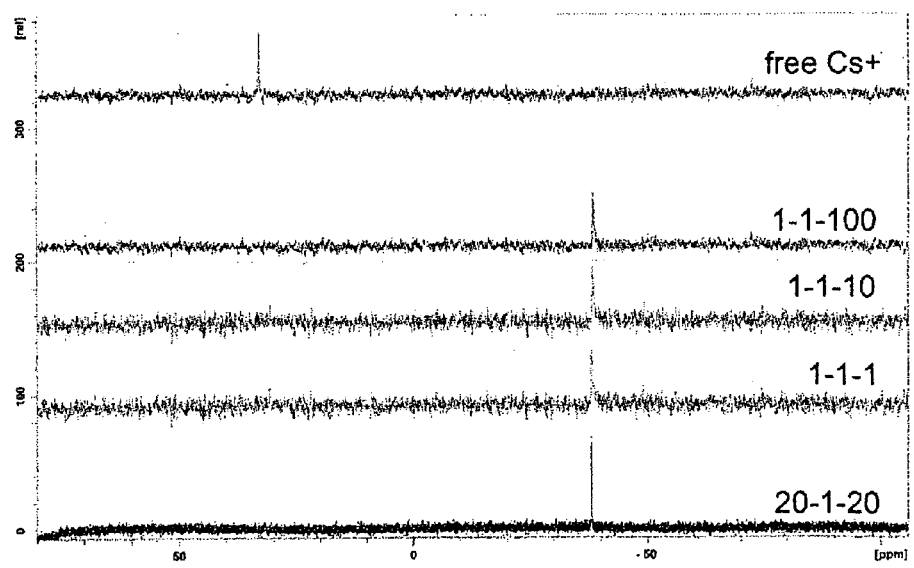
FIG. 6: $Cs^{133}$ NMR spectra.
Figure 7:
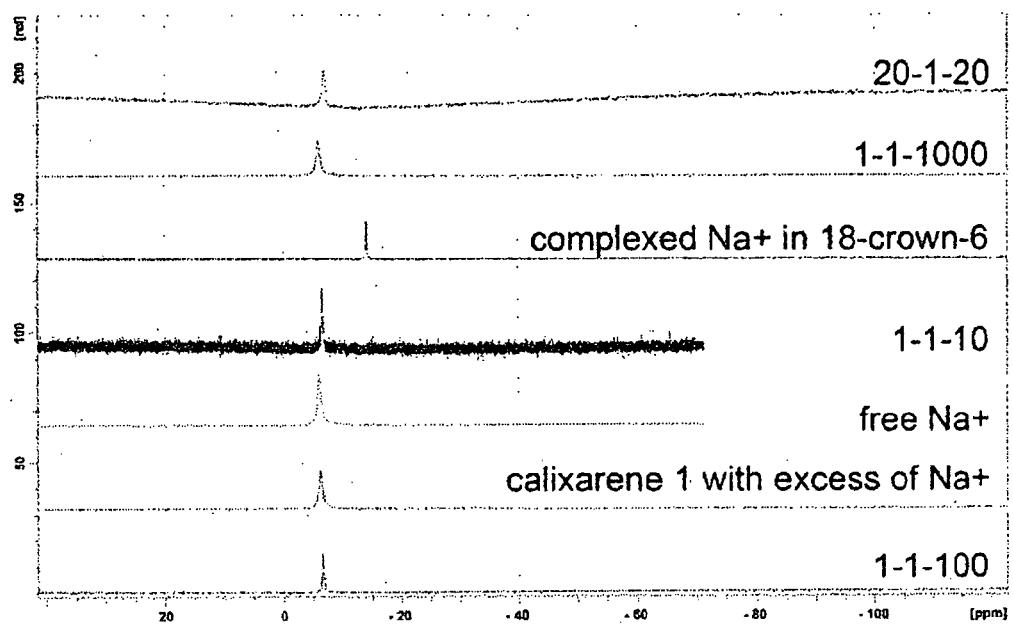
FIG. 7: $Na^{23}$ NMR spectra.

Extraction of Cs by Calixarene 1 from Organic Media in Presence of High Excess of Na Ions: Absolute Selectivity Towards Cs+ Cations The NMR study of competitive complexation of cesium and sodium picrate salts to calixarene 1 was carried out in acetonitrile-d3. Cesium and sodium picrates complexes in $10^{-4}$-$10^{-1}$ concentrations were tested. $Cs^{133}$ and $Na^{23}$ NMR spectra were obtained for samples prepared in 0.6 ml of acetonitrile-d3. Calixarene 1 exhibited absolute selectivity towards Cs+ ions (FIGS. 6 and 7).

TABLE 3

Ratios of Calixarene 1/Cs++/Na+
Cs+ ions in 0.6 mL of acetonitrile-d3.

| Calixarene 1 (molar ratio) | Cs+ (molar ratio) | Na+ (molar ratio) | Sample code |
|---|---|---|---|
| 1 | 1 | 1 | 1-1-1 |
| 1 | 1 | 10 | 1-1-10 |
| 1 | 1 | 100 | 1-1-100 |
| 1 | 1 | 1000 | 1-1-1000 |
| 20 | 1 | 20 | 20-1-20 |
| 0 | 1 | 0 | free Cs+ |
| 0 | 0 | 1 | free Na+ |
| 1 | 0 | 1000 | calixarene 1 with excess of Na+ |

Recycling of the Complexing Structure.

Expulsion of complexed ions may be accomplished by chemical or electrically assisted means.

Example of chemical expulsion: the Cs+ complexed carbon felts 1 and 2 were immersed for 12 h in 3 ml of 0.001 to 1M HCl solution. Then they were washed in demineralized water (30 min), acetonitrile (30 min), dichloromethane (30 min) and dried under vacuum for 1 hour. The XPS analysis indicated the complete absence of Cs+ ions inside and outside in all examined surfaces.

Expulsion by Electrically Assisted Means:

electro-assisted pH-switchable mechanism is shown in the following scheme.

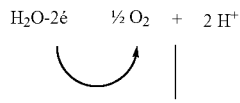

$H_2O - 2\bar{e} \rightarrow \frac{1}{2} O_2 + 2 H^+$

Such a phenomenon within the carbon felts complexed with Cs ions is equivalent to an acidic washing. Such electro-oxidizing strategy was already used to assist the regeneration of copper complexed by basic pyridine groups of the P4VP films by P. Viel et al (Viel, P.; Dubois, L.; Lyskawa, J.; Sallé, M.; Palacin, S. *Applied Surface Science* 2007, 253, 3263-3269.)

Electrochemistry was carried out with a Princeton Applied Research Inc. potentiostat model 263A from EG&G in three-electrode electrochemical cell. The working electrode was Cs complexed carbon felt (1 then 2, see Table 2). The reference electrode was the platinum wire of 0.5 mm in diameter; the counter electrode was the graphite plate. The carbon felts were subjected to anodic treatment in $H_2O$ DI solution of $MgSO_4$, 0.9 g/l during 300 s. A galvanostatic regime with an anode current density of 0.033 mA/cm$^2$ was used for the anodization. The XPS analysis indicated the complete absence of Cs+ ions inside and outside in all examined carbon felts surfaces: the complexing system is reversible.

The recycled carbon felts were reintroduced to selectivity test solution during 12 h at RT in 3 ml glass bottles. Then they were washed in demineralized water during 30 min, acetonitrile (30 min), dichloromethane (30 min) and dried under vacuum for 1 hour. The XPS analysis indicated the presence of Cs+ ions in all examined surfaces: the complexing system is reusable.

A Demonstrator Model for Construction of the Complexing System, Decontamination of Liquid Wastes and Regeneration of the Complexing System.

Figure 8:
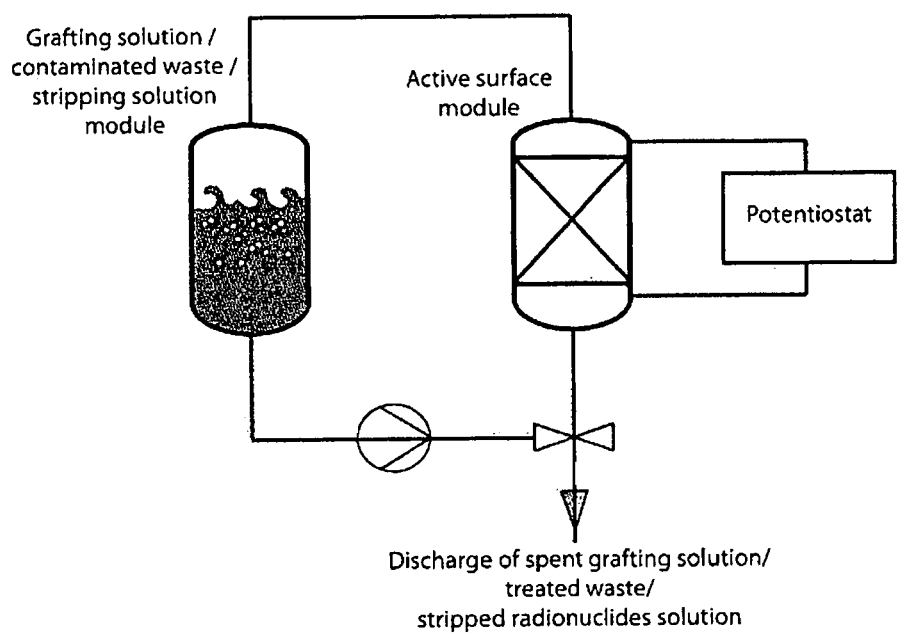
FIG. 8: Simplified scheme of SOLIEX demonstrator model.

A demonstrator model with a total working volume of about 1 liter was constructed to scale-up the SOLIEX process (see FIG. 8) allowing the whole process: construction of the complexing system, decontamination of liquid wastes and regeneration of the complexing felts to be accomplished in situ in the <<active surface module>>. SOLIEX process can be run through the following steps:

i) Preparation of the complexing surface in the active surface module: electrochemical grafting of carbon felts with molecular traps (calixarenes) in the active surface module and further rinsing of the surface from grafting solution;

ii) Passing the waste solution through the complexing system in the active surface module (carbon felt grafted with calixarenes);

iii) On-demand recycling of the complexed radionuclide to make the complexing system available for reuse: contacting the cation-loaded complexing system with a volume of a stripping solution in acidic conditions or electrochemical cation expulsion into the aqueous stripping solution;

iv) Repeating steps i) and ii).

Extraction of Cs by Carbon Felts Containing Calixarene 4 from Water Media.

Three series of grafting/decontamination experiments were carried out for CsNO$_3$ $10^{-4}$-$10^{-5}$ M non-radioactive solutions of 1 L using grafted MERSEN carbon felts; the detected average complexed Cs$^+$ mass was about 9 mg by carbon felt of about 14 g.

The set of carbon felts (diameter of 14 cm) was prepared in the electrochemical cell using 8.8 g of TEAP (supporting electrolite) and 212 mg of calixarene 4 solution in 1 L of acetonitrile by circulating flow of the left module. The carbon felts were then washed by flow of acetonitrile and water to remove the non-grafted calixarene molecules. Three batches of 1 L of initial $10^{-4}$ M cesium aqueous solution were prepared using commercially available cesium nitrate to accomplish the decontamination tests.

The batches were then circulated through the carbon felts located in the electrochemical cell.

Figure 9:
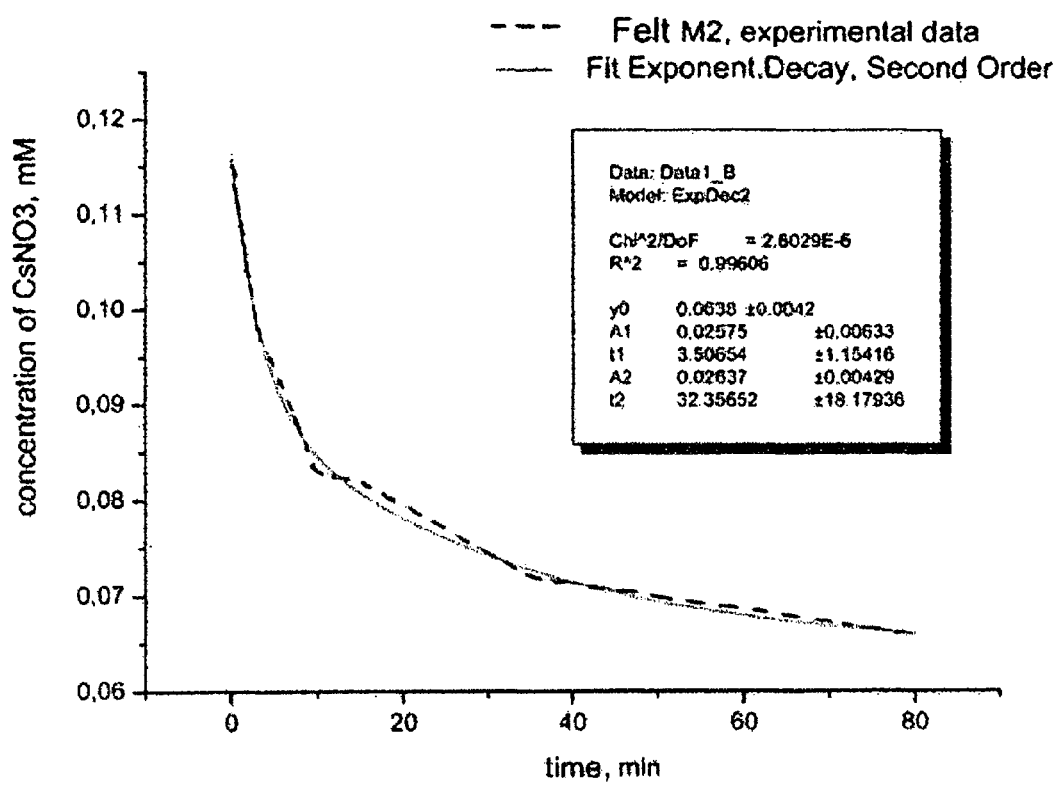
FIG. 9: Extraction of Cs by carbon felts containing calixarene 4 from water media.

Atomic absorption spectroscopy (AAS) was successfully implemented for analysis of Cs solutions before and after extraction process to estimate the complexing capacity of carbon felts. The set of the decontamination experiments was accomplished; the initial and resulting concentrations of cesium nitrate solutions are presented in table below and on FIG. 9:

| Initial Solution, mM | 3 min | 5 min | 10 min | 15 min | 20 min | 35 min | 50 min | 80 min |
|---|---|---|---|---|---|---|---|---|
| 0.1157 | 0.103 | 0.0941 | 0.0898 | 0.0811 | 0.0820 | 0.0728 | 0.0687 | 0.0680 |
| 0.1092 | 0.0935 | 0.0940 | 0.0878 | 0.0841 | 0.0824 | 0.0742 | 0.0727 | 0.0659 |
| 0.1098 | 0.0971 | 0.0941 | 0.0843 | 0.0803 | 0.0820 | 0.0760 | 0.0705 | 0.0637 |
| Average concentrations: 0.116 | 0.098 | 0.094 | 0.0873 | 0.082 | 0.0822 | 0.072 | 0.0706 | 0.0659 |

REFERENCES

[1] K. Shakir, M. Sohsah, M. S. (1957). Removal of cesium from aqueous solutions and radioactive waste simulants by coprecipitate flotation. *Separation and Purification Technology*, 54(3), 373-381.

[2] Shakir, K., Ghoneimy, H. F., Beheir, S. G., & Refaat, M. (2007). Flotation of Cesium Coprecipitated with Nickel Hexacyanoferrate(II) from Aqueous Solutions and Radioactive Waste Simulants. *Separation Science and Technology*, 42(6), 1341-1365. Taylor & Francis.doi: 10.1080/01496390601174257

[3] Warin, D. (2007). Status of the French research program on partitioning and transmutation. *Journal of Nuclear Science and Technology* ( ), 44(3), 410-414.

[4] Warin, D. (2010). Future nuclear fuel cycles: Prospect and challenges for actinide recycling. *IOP Conference Series: Materials Science and Engineering*, 9, 012063.

[5] D. Bélanger and J. Pinson, *Chem. Soc. Rev* 2011, 40, 3995-4048

[6] J. Lyskawa, F. Le Derf, E. Levillain, M. Mazari, M. Sallé, L. Dubois, P. Viel, C. Bureau, and S. Palacin, *J. Am. Chem. Soc.*, 2004, 126 (39), pp 12194-12195

The invention claimed is:

1. A complexing system for extracting a radionuclide from a waste solution comprising calixarene groups covalently bonded to the surface of a porous conducting material, n being equal to 4, 6 or 8, provided that the porous conducting material is not a dispersable and/or particulate material.

2. The method of claim 1, wherein the porous conducting material is a conducting-fiber material.

3. The complexing system of claim 2, wherein the conducting-fiber material is a carbon-fiber material.

4. The complexing system of claim 3, wherein the carbon-fiber material is selected from carbon felts.

5. The complexing system of claim 1, wherein the calixarene groups are covalently bonded via —C(=O)NH—, —NH—C(=O)—, or —C—C.

6. The complexing system of claim 1, wherein the calixarene group is a calixarene-crown ether group.

7. The complexing system of claim 1, wherein the calixarene group is calixarene-crown-6 ether group.

8. The complexing system of claim 1, wherein the calixarene group is a 1,3-alternate calixarene-crown-6 conformer group.

9. A method for preparing the complexing system of claim 1 comprising:
   i) activating a porous conducting material by applying an electric potential sufficient to allow the grafting of a radical precursor group;
   ii) reacting the activated porous conducting material with a compound of formula (II), thereby obtaining a modified porous conducting material;

$$W-L-V \quad (II)$$

wherein

V is a radical precursor group;

W is selected from the group consisting of F, Cl, Br, I, OH, $NHR_{10}$, C(=O)H, C(=O)Hal and C(=O)$OR_9$, L is spacing group and selected from —$(CH_2)_r$—, $C_3$-$C_{10}$ cycloalkylene or $C_3$-$C_{10}$ arylene, $R_9$, $R_{10}$ are each independently selected from H or ($C_1$-$C_6$) alkyl, r is an integer selected from 1 to 20;
   iii) grafting the modified porous conducting material with a compound of formula (Ia):

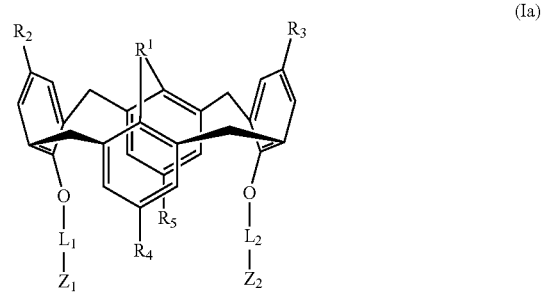

wherein:

$R_1$ is selected from the group consisting of —X($C_2H_4X$)$_m$— and —X($C_2H_4X$)$_{p/2}$YX($C_2H_4X$)$_{p/2}$—;

X is independently O or NH;

m=3, 4, 5 or 6;

p=2 or 4;

Y is $C_3$-$C_{10}$ cycloalkylene or $C_6$-$C_{10}$ arylene;

$R_2$-$R_5$ are each independently H or $C_1$-$C_6$ alkyl;

$L_1$, $L_2$ are spacing groups and are each independently selected from the group consisting of —$(CH_2)_q$—, $C_3$-$C_{10}$ cycloalkylene and $C_3$-$C_{10}$ arylene;

$Z_1$, $Z_2$ are grafting groups and are each independently selected from the group consisting of F, Cl, Br, I, $OHNH_2$, C(=O)H, C(=O)Hal and C(=O)$OR_8$;

$R_8$ is independently H or ($C_1$-$C_6$) alkyl;

q is an integer ranging from 1 to 12.

10. A method for preparing the complexing system of claim 1 comprising the steps of:
   i) activating a porous conducting material by applying on the material an electric potential sufficient to allow the grafting of a radical precursor group;
   ii) grafting the activated material with a compound of formula (Ib),

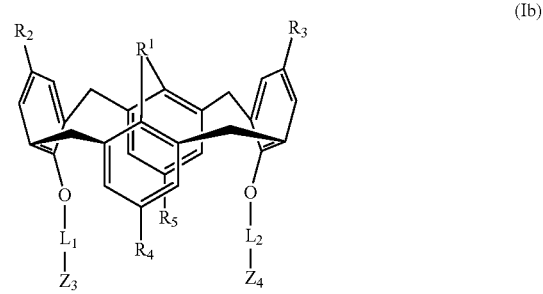

wherein $R_1$ is selected from that group consisting of —X($C_2H_4X$)$_m$— and —X($C_2H_4X$)$_{p/2}$YX($C_2H_4X$)$_{p/2}$—;

X is independently O or NH;

m=3, 4, 5 or 6;

p=2 or 4;

Y is $C_3$-$C_{10}$ cycloalkylene or $C_6$-$C_{10}$ arylene;

$R_2$-$R_5$ are each independently H or $C_1$-$C_6$ alkyl;

$L_1$, $L_2$ are spacing groups and are each independently selected from the group consisting of —$(CH_2)_q$—, $C_3$-$C_{10}$ cycloalkylene and $C_3$-$C_{10}$ arylene;

$Z_3$, $Z_4$ are each independently a group M-L-V,

M is independently O or $NR_{10}$;

L is spacing group selected from the group consisting of —$(CH_2)_r$—, $C_3$-$C_{10}$ cycloalkylene and $C_3$-$C_{10}$ arylene;

V is a radical precursor group;

$R_{10}$ is H or ($C_1$-$C_6$) alkyl.

11. A method for extracting radionuclides from a waste solution, said method comprising the step of:
  i) contacting a volume of a waste solution with the complexing system according to claim 1; optionally
  ii) contacting the complexing system containing a portion of radionuclide obtained at step i), with a volume of a stripping solution in acidic conditions,
  thereby removing the complexed radionuclide from said complexing system into the stripping solution, to make the complexing system available for reuse; and optionally
  iii) repeating steps i) and ii).

12. The method of claim 11, wherein the radionuclides are cesium and/or strontium.

13. The method of claim 11, wherein the waste solution is charged with competing alkali metal cations.

14. The method of claim 11, wherein the acidic conditions in step ii) are obtained by applying an electric potential difference on the porous conducting material of the complexing system.

* * * * *